US008622946B2

(12) United States Patent
Ingimundarson et al.

(10) Patent No.: US 8,622,946 B2
(45) Date of Patent: Jan. 7, 2014

(54) ANKLE BRACE

(75) Inventors: Arni Thor Ingimundarson, Ladera Ranch, CA (US); Palmi Einarsson, San Juan Capistrano, CA (US)

(73) Assignee: Ossur HF, Reykjavik (IS)

( * ) Notice: Subject to any disclaimer, the term of this patent is extended or adjusted under 35 U.S.C. 154(b) by 908 days.

(21) Appl. No.: 12/628,254

(22) Filed: Dec. 1, 2009

(65) Prior Publication Data
US 2010/0137770 A1 Jun. 3, 2010

Related U.S. Application Data

(60) Provisional application No. 61/237,739, filed on Aug. 28, 2009, provisional application No. 61/119,116, filed on Dec. 2, 2008.

(51) Int. Cl.
A61F 5/00 (2006.01)
(52) U.S. Cl.
USPC .............................. 602/27; 602/65; 128/882
(58) Field of Classification Search
USPC ............... 602/27–29, 65–66; 128/882; 36/89, 36/140, 142
See application file for complete search history.

(56) References Cited

U.S. PATENT DOCUMENTS

| 1,318,290 | A | 6/1921 | Diadul |
| 3,674,023 | A | 7/1972 | Mann |
| 3,713,437 | A | 1/1973 | Wiedmer |
| 3,732,861 | A | 5/1973 | Lehneis |
| 4,280,488 | A | 7/1981 | Polsky et al. |
| 4,280,489 | A | 7/1981 | Johnson, Jr. |
| 4,446,856 | A | 5/1984 | Jordan |
| 4,497,070 | A | 2/1985 | Cho |
| 4,510,927 | A | 4/1985 | Peters |
| 4,517,968 | A | 5/1985 | Greene et al. |
| 4,628,945 | A | 12/1986 | Johnson, Jr. |
| 4,630,600 | A * | 12/1986 | Spencer et al. ............... 602/27 |
| 4,646,726 | A | 3/1987 | Westin et al. |
| 4,651,726 | A | 3/1987 | Holland |

(Continued)

FOREIGN PATENT DOCUMENTS

AU    37277/93 B    9/1993
EP    619 102 B1    7/2001

(Continued)

OTHER PUBLICATIONS

International Search Report and Written Opinion issued in PCT/US2009/006327, Apr. 20, 2010.

(Continued)

Primary Examiner — Patricia Bianco
Assistant Examiner — Kari Petrik
(74) Attorney, Agent, or Firm — Workman Nydegger

(57) ABSTRACT

The ankle brace includes a calf body defining lateral and medial frontal sides spaced by a frontal opening, and first and second straps depending from the first and second frontal sides of the calf body, respectively. The first and second straps are arranged to extend juxtaposed across the opening and secure to the second and first frontal sides, respectively. The brace also includes opposed lateral and medial ankle struts pivotally attached to the calf body, and a footplate connected to the ankle struts. The medial ankle strut has greater rigidity than the lateral ankle strut. The calf body medial section has greater rigidity than the calf body lateral section.

20 Claims, 13 Drawing Sheets

(56) References Cited

U.S. PATENT DOCUMENTS

| | | | |
|---|---|---|---|
| 4,724,847 A | 2/1988 | Nelson | |
| 4,825,856 A | 5/1989 | Nelson | |
| 4,834,078 A | 5/1989 | Biedermann | |
| 4,865,023 A | 9/1989 | Craythorne et al. | |
| 4,870,725 A * | 10/1989 | Dubowik | 24/442 |
| 4,934,355 A | 6/1990 | Porcelli | |
| RE33,395 E | 10/1990 | Peters | |
| 4,966,134 A | 10/1990 | Brewer | |
| 4,977,891 A | 12/1990 | Grim | |
| 5,031,607 A | 7/1991 | Peters | |
| 5,050,620 A | 9/1991 | Cooper | |
| 5,088,478 A | 2/1992 | Grim | |
| 5,094,232 A | 3/1992 | Harris et al. | |
| D326,719 S | 6/1992 | Eghamn | |
| 5,125,400 A | 6/1992 | Johnson, Jr. | |
| 5,177,884 A | 1/1993 | Rullier | |
| 5,209,722 A * | 5/1993 | Miklaus et al. | 602/27 |
| 5,217,431 A | 6/1993 | Toronto et al. | |
| D338,066 S | 8/1993 | Baron | |
| 5,242,379 A | 9/1993 | Harris et al. | |
| 5,348,530 A | 9/1994 | Grim et al. | |
| 5,366,439 A | 11/1994 | Peters | |
| 5,445,602 A | 8/1995 | Grim et al. | |
| 5,496,263 A | 3/1996 | Fuller, II et al. | |
| 5,501,659 A | 3/1996 | Morris et al. | |
| 5,527,269 A | 6/1996 | Reithofer | |
| 5,577,998 A | 11/1996 | Johnson, Jr. et al. | |
| 5,613,941 A | 3/1997 | Prengler | |
| 5,676,642 A | 10/1997 | Peters | |
| D394,112 S | 5/1998 | Duback et al. | |
| 5,778,563 A | 7/1998 | Ahlbaumer | |
| 5,795,316 A | 8/1998 | Gaylord | |
| 5,797,865 A | 8/1998 | McDavid, III | |
| 5,836,903 A | 11/1998 | Peters | |
| 5,853,381 A | 12/1998 | Stevenson et al. | |
| 5,868,693 A | 2/1999 | Duback et al. | |
| 5,902,259 A | 5/1999 | Wilkerson | |
| 5,944,678 A | 8/1999 | Hubbard | |
| 5,951,504 A * | 9/1999 | Iglesias et al. | 602/27 |
| 5,971,946 A | 10/1999 | Quinn et al. | |
| 6,024,712 A | 2/2000 | Iglesias et al. | |
| 6,053,884 A | 4/2000 | Peters | |
| 6,083,185 A | 7/2000 | Lamont | |
| 6,126,625 A | 10/2000 | Lundberg | |
| 6,146,350 A | 11/2000 | Morton | |
| D436,177 S | 1/2001 | Miller | |
| 6,350,246 B1 | 2/2002 | DeToro et al. | |
| 6,394,971 B1 | 5/2002 | Slautterback et al. | |
| 6,398,750 B1 | 6/2002 | Quinn et al. | |
| 6,524,266 B1 | 2/2003 | Peters | |
| 6,602,215 B1 | 8/2003 | Richie, Jr. | |
| 6,656,145 B1 | 12/2003 | Morton | |
| 6,689,081 B2 | 2/2004 | Bowman | |
| 6,749,578 B2 | 6/2004 | Peters | |
| 6,767,332 B1 | 7/2004 | Pardue et al. | |
| 6,858,017 B2 | 2/2005 | Peters | |
| 6,875,190 B2 | 4/2005 | Reinhardt | |
| 6,964,663 B2 | 11/2005 | Grant et al. | |
| D527,829 S | 9/2006 | Dodo et al. | |
| 7,115,105 B2 | 10/2006 | Cropper | |
| D552,743 S | 10/2007 | Verkade et al. | |
| D552,744 S | 10/2007 | Verkade et al. | |
| 7,288,076 B2 | 10/2007 | Grim et al. | |
| 7,364,561 B1 | 4/2008 | Morton | |
| 7,370,442 B2 | 5/2008 | Jung et al. | |
| 7,429,254 B1 | 9/2008 | Engelman | |
| 7,524,295 B1 | 4/2009 | Peters et al. | |
| D596,301 S | 7/2009 | Campos et al. | |
| 7,572,241 B2 | 8/2009 | Slautterback et al. | |
| 7,615,026 B1 | 11/2009 | Peters et al. | |
| 7,713,224 B1 | 5/2010 | Peters et al. | |
| D618,359 S | 6/2010 | Einarsson | |
| D619,726 S | 7/2010 | Win | |
| D620,124 S | 7/2010 | Einarsson | |
| 8,043,245 B2 | 10/2011 | Campos et al. | |
| D649,650 S | 11/2011 | Wehsely-Swiczinsky | |
| 2001/0056251 A1 | 12/2001 | Peters | |
| 2002/0029009 A1 | 3/2002 | Bowman | |
| 2003/0014001 A1 | 1/2003 | Martin | |
| 2003/0158506 A1 | 8/2003 | Hinshon | |
| 2003/0171703 A1 | 9/2003 | Grim et al. | |
| 2004/0167453 A1 | 8/2004 | Peters | |
| 2004/0225242 A1 | 11/2004 | Lidolt et al. | |
| 2005/0096576 A1 | 5/2005 | Castro | |
| 2005/0165338 A1 | 7/2005 | Iglesias et al. | |
| 2006/0084899 A1 * | 4/2006 | Verkade et al. | 602/27 |
| 2006/0135901 A1 * | 6/2006 | Ingimundarson et al. | 602/26 |
| 2007/0027420 A1 | 2/2007 | Yu | |
| 2007/0060854 A1 | 3/2007 | Cropper | |
| 2007/0213649 A1 | 9/2007 | Gaylord | |
| 2010/0137770 A1 | 6/2010 | Ingimundarson et al. | |
| 2012/0078148 A1 | 3/2012 | Hu et al. | |

FOREIGN PATENT DOCUMENTS

| | | |
|---|---|---|
| FR | 2 766 359 | 7/1998 |
| WO | 93/06797 | 4/1993 |
| WO | 2006/041992 A3 | 4/2006 |

OTHER PUBLICATIONS

Veolcity™ Ankle Brace, Product Information Brochure, Mar. 1, 2010, 2 pages.

T1 Trainer Active Ankle Brace, Product Information from website www.activeankle.com, Jun. 26, 2008, 1 page.

Active Ankle—T2 Product Information from website www.activeankle.com, Jun. 26, 2008, 1 page.

Chameleon brace product information from website www.getchamelon.com, Jun. 26, 2008, 1 page.

Step Smart® product information brochure, Jun. 26, 2008, 2 pages.

Swedeo-O Arch Lok® product information from website: www.swedo.com/arch.htm, Jun. 26, 2008, 1 page.

Sure Step Fixed Position Ankle Brace, product information from website: www.ankleshop.com/proddetail.asp?prod=A382XX, Jun. 26, 2008, 1 page.

Bledsoe SideKick Ankle Brace product information brochure, Mar. 1, 2010.

Bledsoe Ultimate Ankle Brace product information brochure, Mar. 1, 2010.

BREG product information brochure, Jun. 26, 2008.

\* cited by examiner

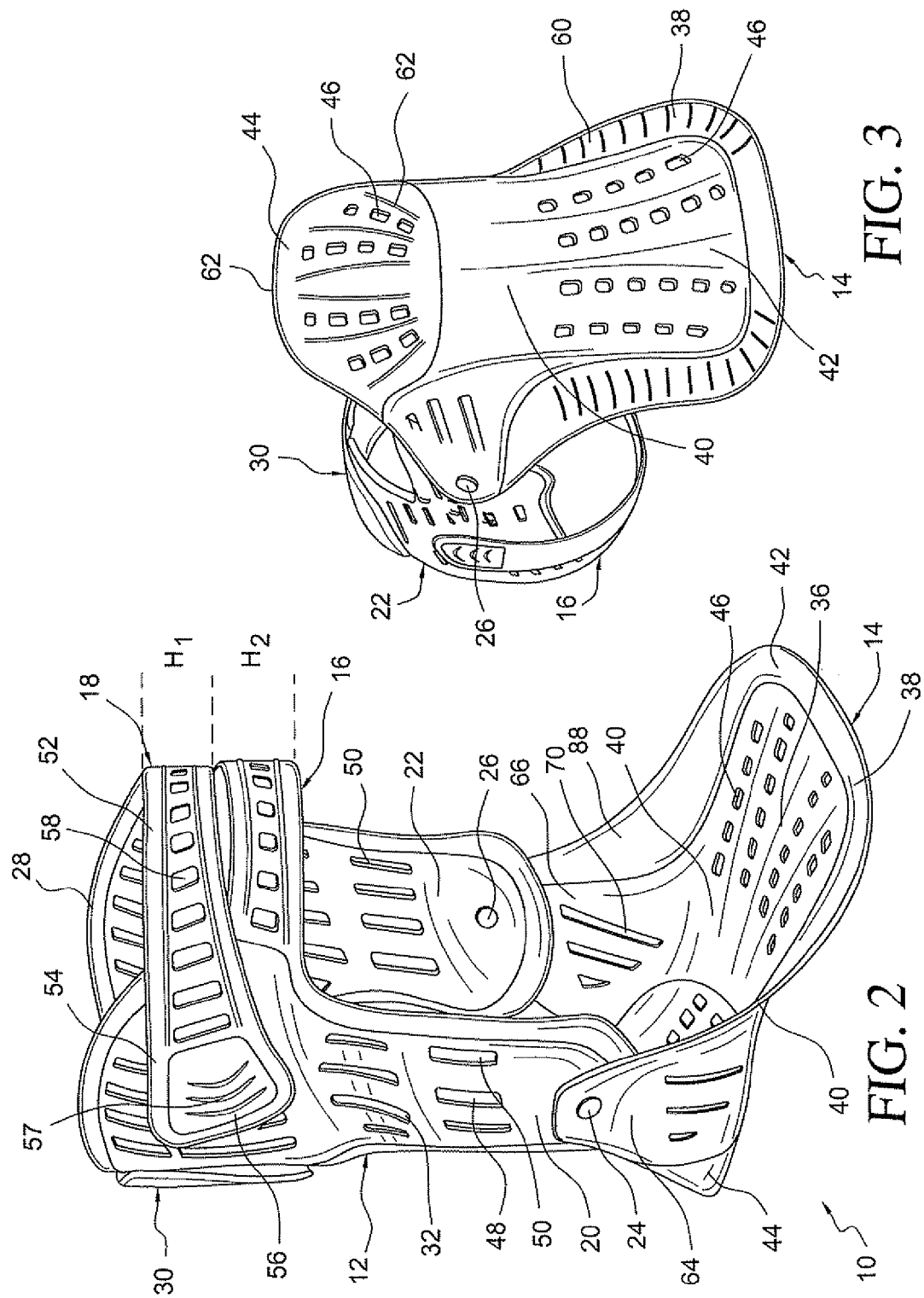

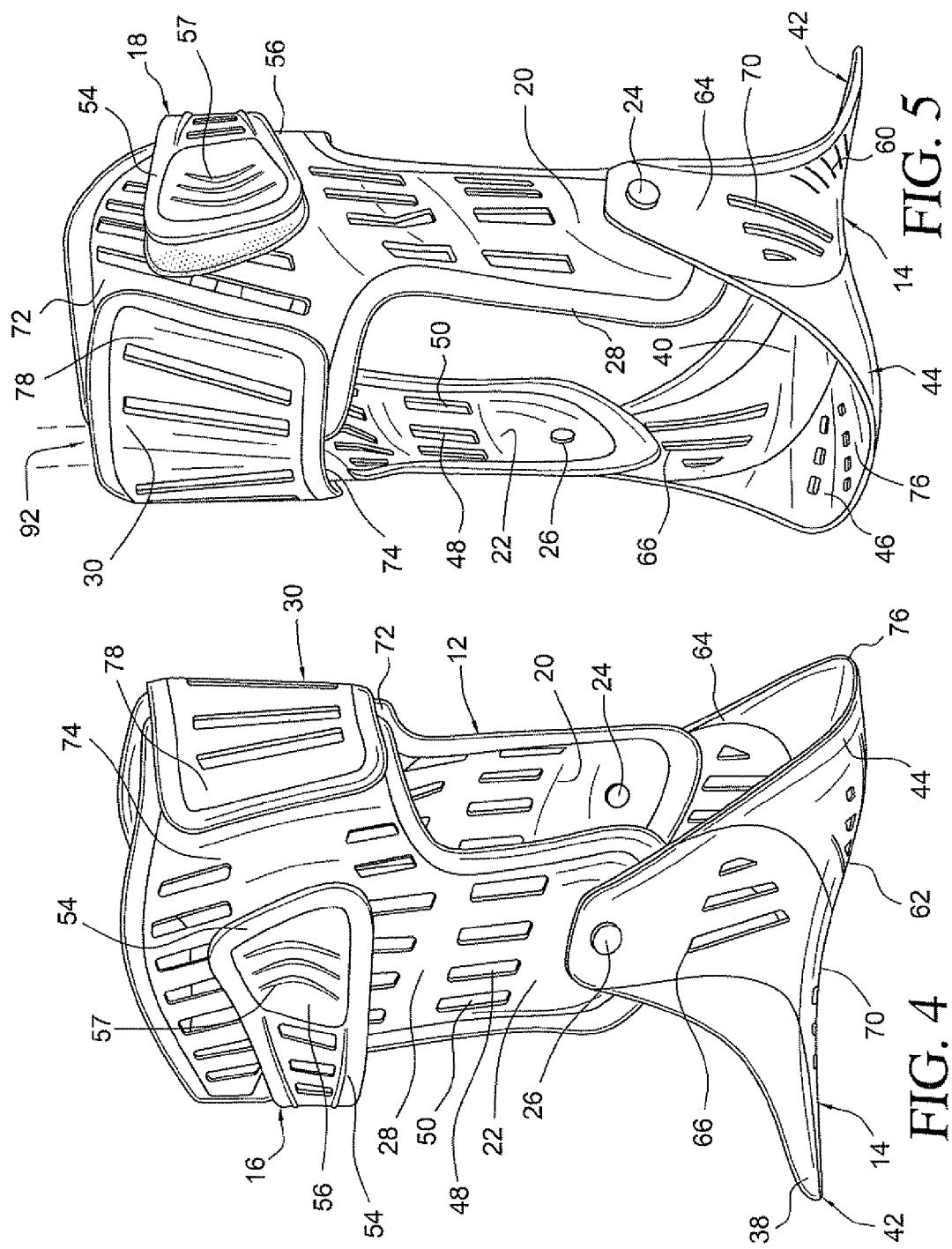

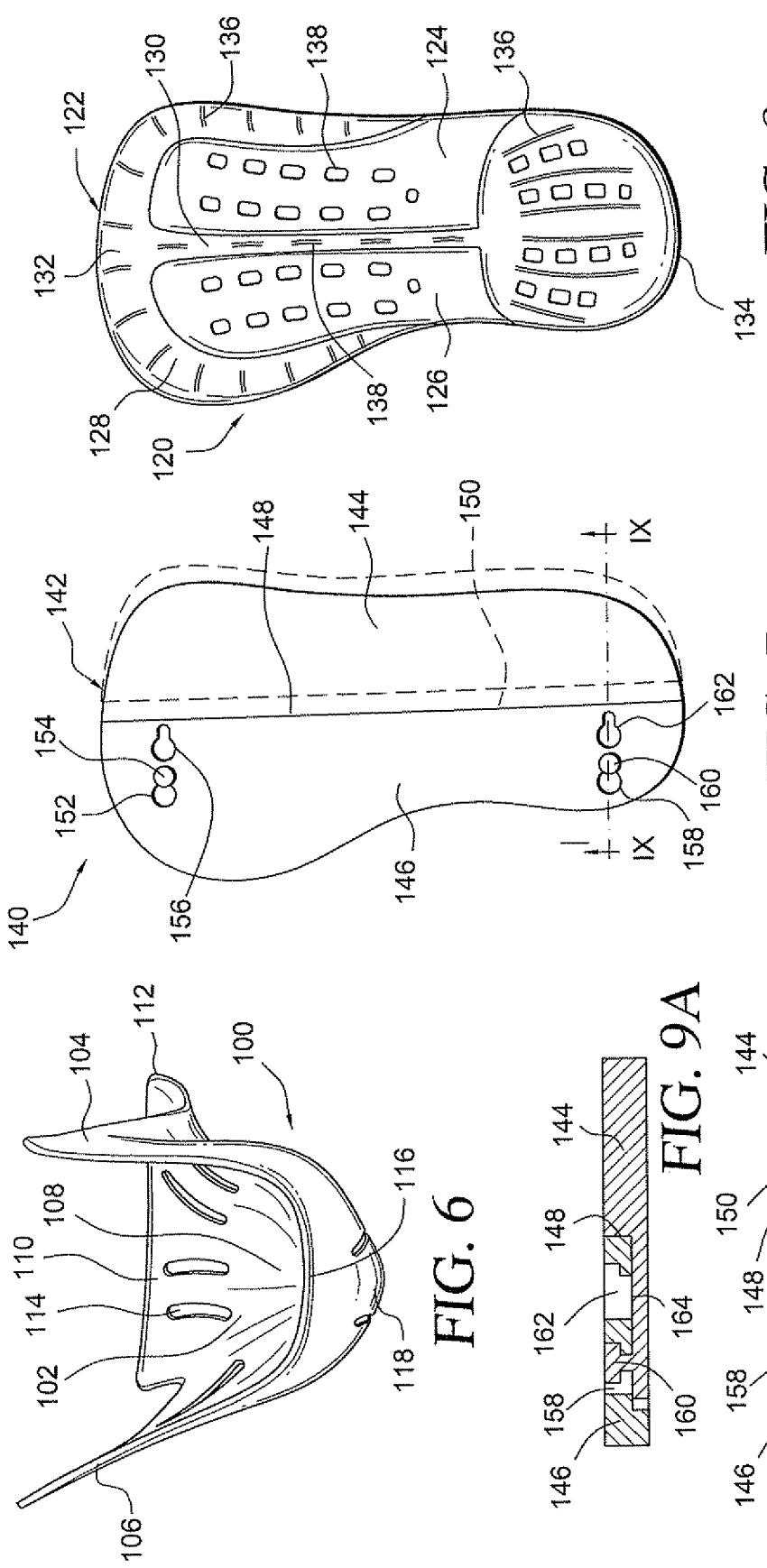

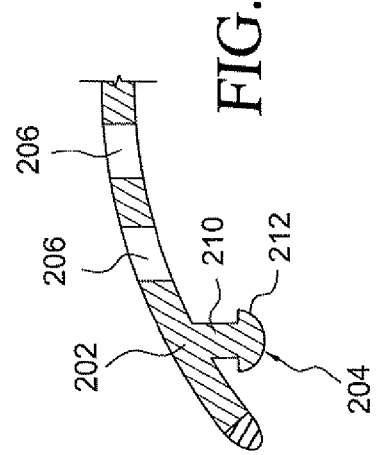
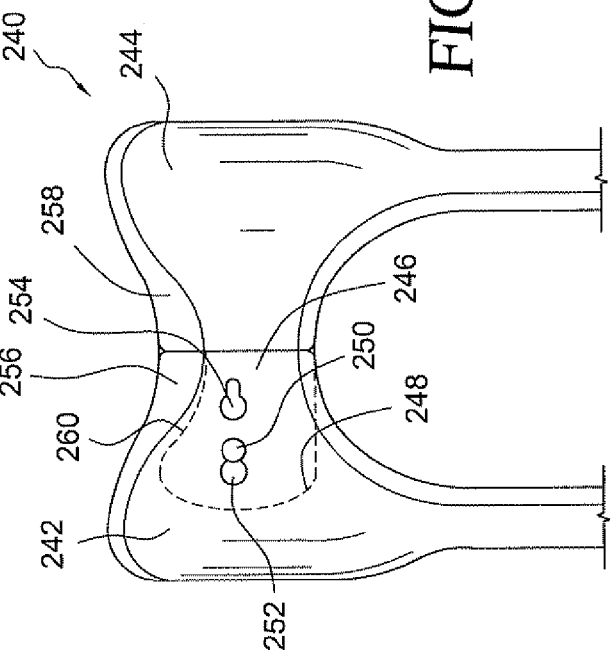
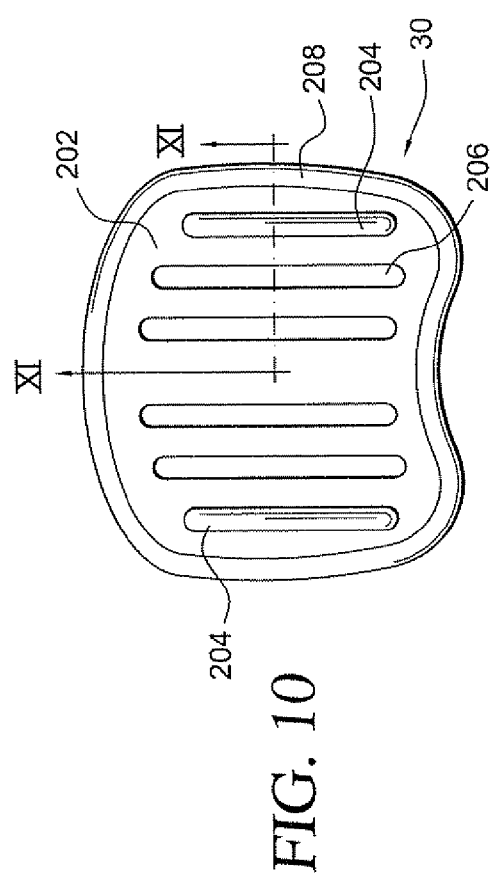
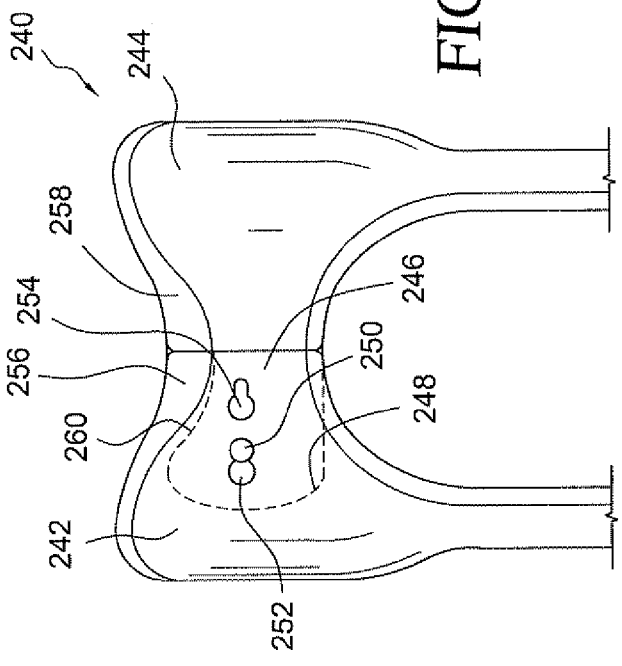

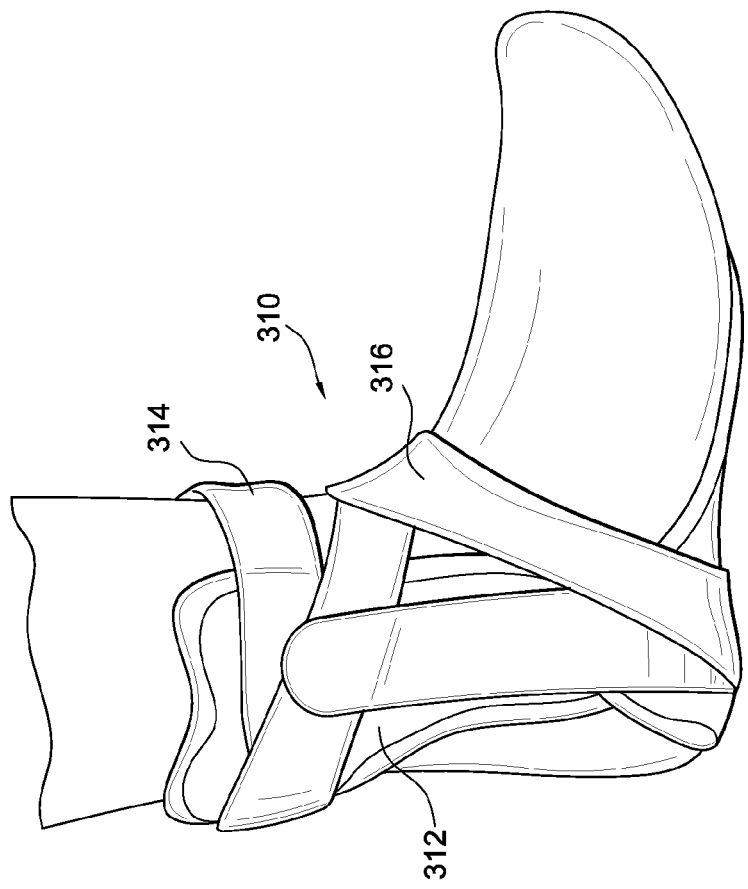
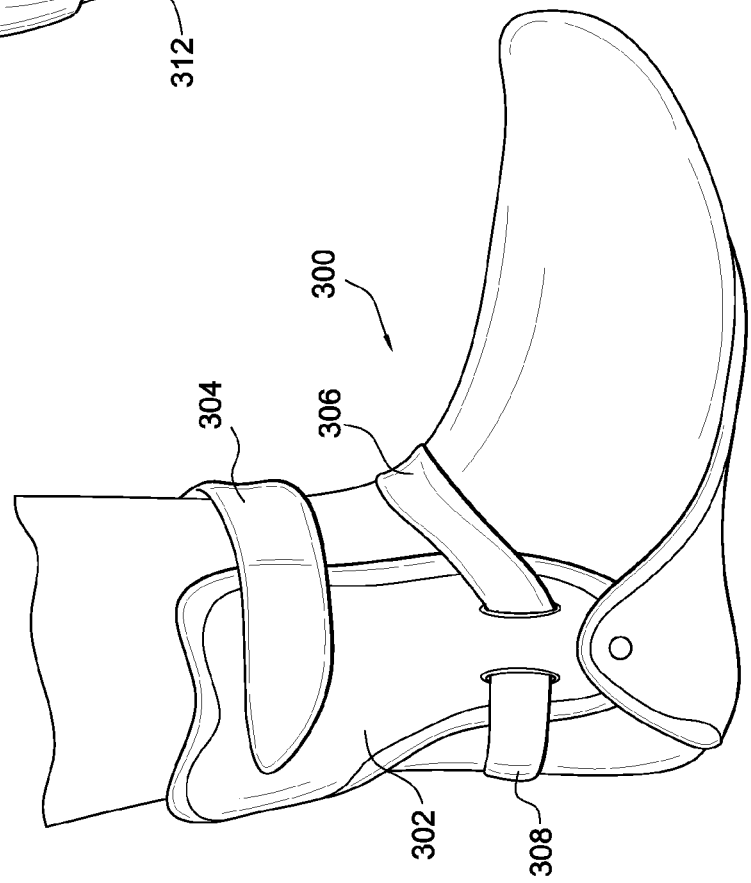

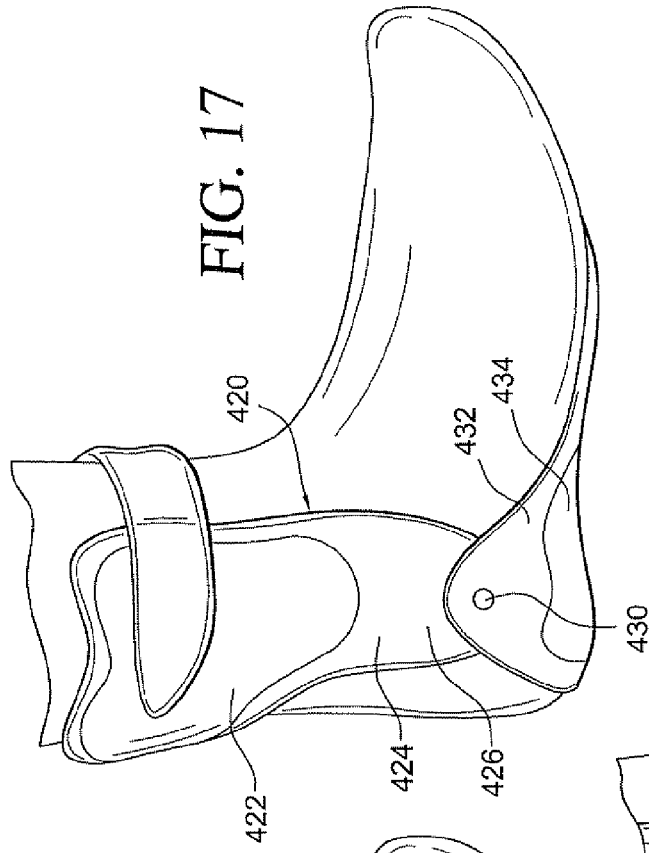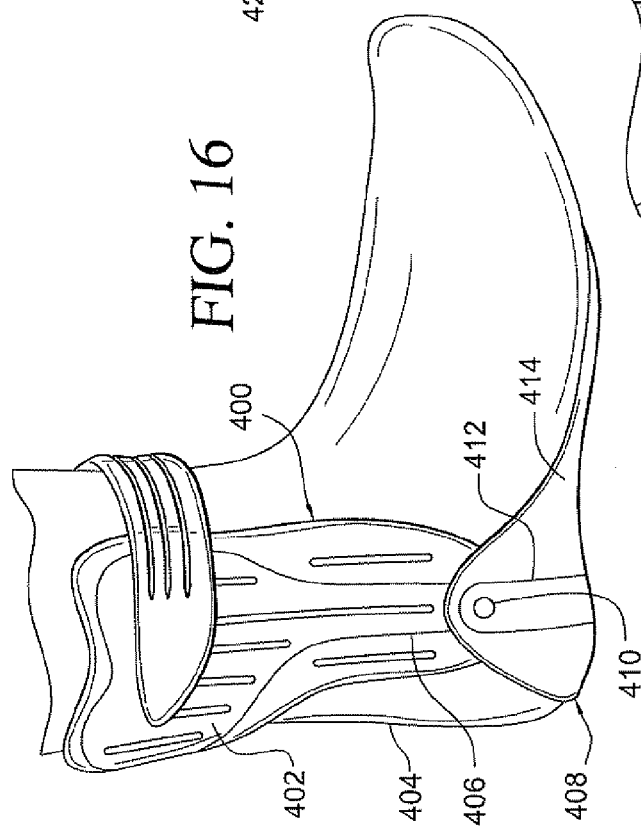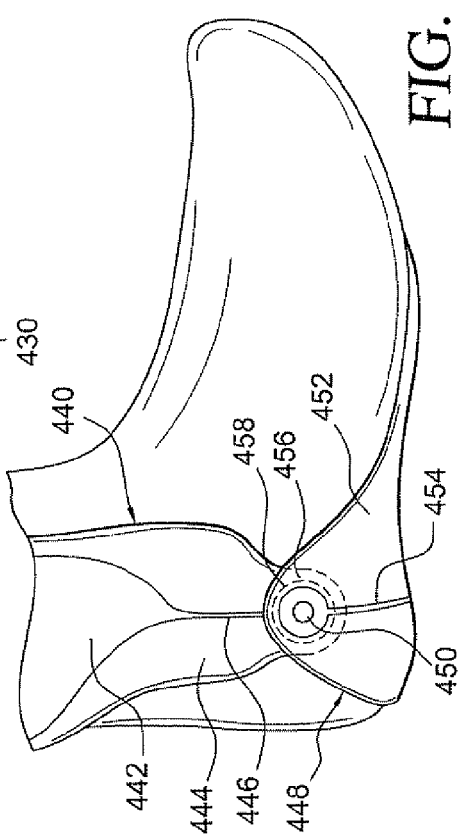

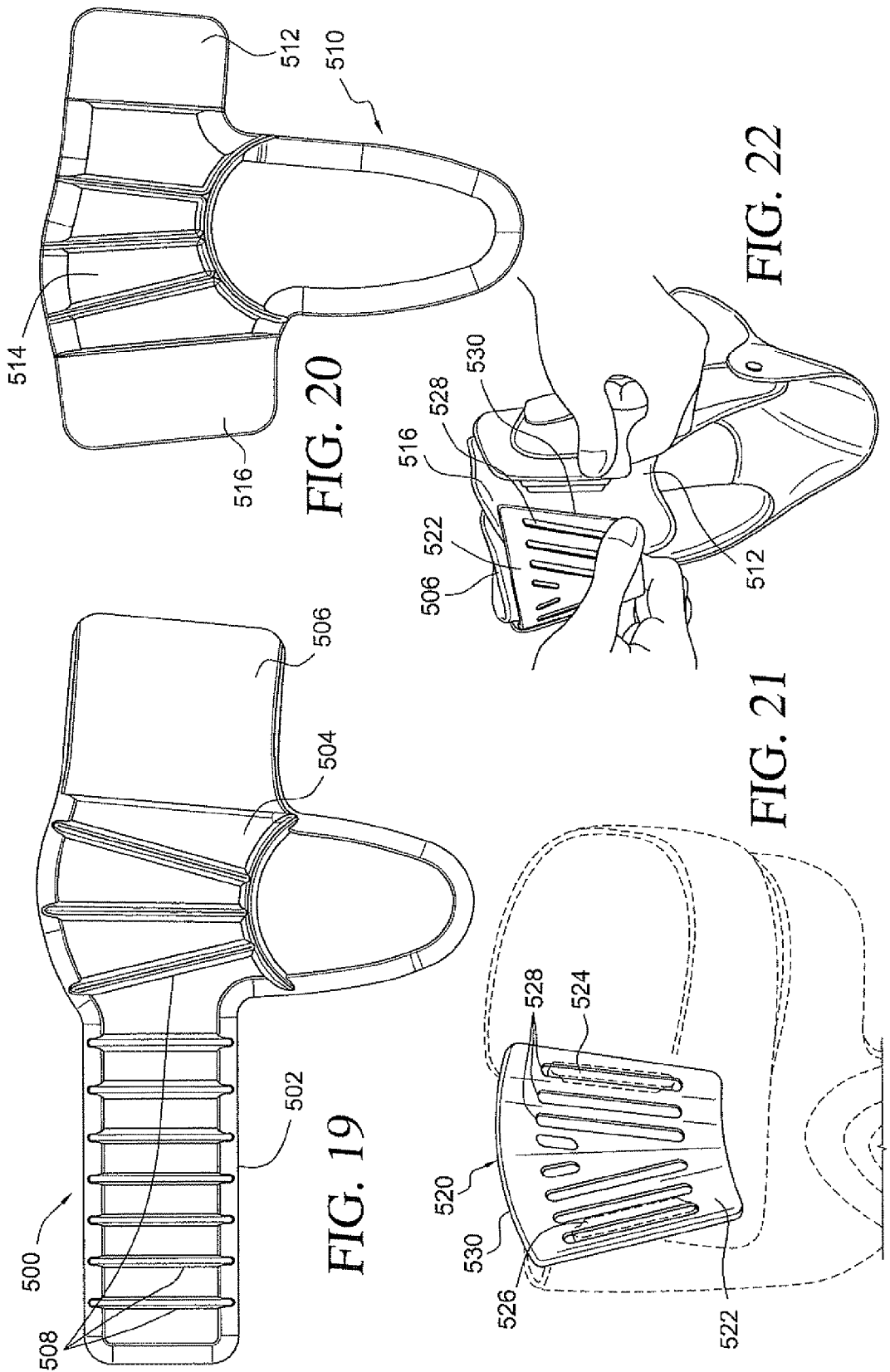

ANKLE BRACE

CROSS-REFERENCE TO RELATED APPLICATIONS

This application claims the benefit of U.S. provisional application 61/119,116, filed on 2 Dec. 2008, and U.S. provisional application 61/237,739, filed on 28 Aug. 2009, both of which are incorporated herein by reference.

FIELD OF INVENTION

The application is directed orthopedic devices and supports, and more particularly embodied herein as an ankle brace.

BACKGROUND

Ankle braces and supports are designed to provide warmth, compression and support to mild to moderate ankle strains and sprains. These braces typically accommodate an ankle so that the wearer can continue with daily activities despite injury. Such ankle braces may also be arranged to offer additional support in preventing or in post injury situations whether the brace is adapted for daily walking or participating in physical activities.

Many of these ankle braces give medial and lateral control of an ankle while allowing for normal dorsi and plantar flexion. These types of braces are also adapted for mild to moderate sprains, such as Grade I-III and high ankle sprains, strains, post cast support, proprioceptive deficit from previous traumatic injury, and injury prevention such as chronic ankle instability after rehabilitation is completed.

A hinged ankle brace usually offers superior support and stability compared to elastic or neoprene braces. These hinged ankle braces are dynamic braces in that they move as the ankle moves and contain various means to accommodate such movement. Many hinged braces are used for people who suffer from medial or lateral instability of the ankle, and these braces may also be tailored to addressing acute injuries following cast immobilization or after the use of a walking boot.

SUMMARY

The inventive orthopedic brace embodiments described herein are exemplified in the context of an ankle brace having at least the following objectives which serve as improvements over known ankle brace, providing greater functionality and support. These objectives include: (1) an anatomical footplate providing longitudinal arch support, (2) a brace hinged at the ankle to allow unrestricted dorsi-plantar range of motion, (3) an offset joint axis to match medial and lateral malleolus heights, (4) posterior width adjustment, (5) easy application of the brace, and (6) pain free application of brace such that no plantar flexion is required for a swollen ankle application, and (7) modular strapping configurations.

The orthopedic device as exemplified as an ankle brace includes certain inventive features which are differentiated from known ankle braces. The features include but are not limited to:

a. width adjustability to reduce the inventory of customers stocking products with multiple widths;
b. width extender accessory to add-on to the product for patients with plus size calves;
c. simple dual straps to ease donning and doffing so that the patient won't need to thread straps through D-rings or each other;
d. anti-slip texture under footplate to prevent rotation between the product and the shoe;
e. additional strapping for extra support;
f. allowing for open-front donning and doffing;
g. configurable for receiving modular strapping systems for different strap formations for varying levels of support;
h. liners that conform to anatomy and reduce creasing/bunching;
i. ribs on the medial and lateral struts to add reinforcement where inversion tends to cause the product to buckle and bow;
j. ventilation formed on shells for breathability and to provide flexibility in one direction (to conform around the anatomy), but strength in the other direction (to resist inversion and eversion); and
k. heel cup designed to capture the calcaneous and more firmly fit the foot.

In accordance with an embodiment of invention, the ankle brace includes a calf body defining first and second frontal sides spaced by a frontal opening, and first and second straps depending from the first and second frontal sides of the calf body, respectively. The first and second straps are arranged to extend juxtaposed across the opening and secure to the second and first frontal sides, respectively. The brace also includes opposed ankle struts pivotally attached to the calf body, and a footplate connected to the ankle struts.

In a variation, the calf body defines a shell portion and a peripheral edge portion secured to the shell portion. The shell portion has greater rigidity than the peripheral edge portion.

In another variation of the straps, the first and second straps are continuously and unitarily formed from the peripheral edge portion or, alternatively, the first and second straps are continuously and unitarily formed from a peripheral edge portion of the calf body.

The first and second straps may define a strap body and a handle with the handle being integrally molded into the strap body. The strap body may be formed from a material more resilient than a material used to forum the handle. The handle can define a grip pattern. The first and second straps also may define a plurality of apertures.

In yet another variation, the first and second straps are arranged generally parallel heightwise relative to one another about the opening. The first and second straps may have generally corresponding profiles with the first and second straps having first and second heights, respectively, forming a combined strap height greater than the first and second heights when the first and second straps secure to the second and first frontal sides, respectively. The first strap depends from the first frontal side at a location higher relative to the footplate than a location from which the second strap depends from the second frontal side.

According to another embodiment, the ankle brace has first and second calf shells which define first and second frontal sides bordering and spaced apart by a frontal opening. The first and second rear sides are spaced apart from one another. An expansion coupling removably secures to and bridges the first and second rear sides at a plurality of locations.

In a variation, the coupling system includes an expansion part defining opposed series of diagonal slots, such that there are first and second series of slot arranged obliquely relative to one another. Each of the calf body rear sides form a tab on an inner surface thereof which extend toward one another. These tabs are arranged to engage and secure with one of the slots for size adjustment of the calf portion of the ankle brace.

The oblique arrangement of the slots allows for the calf bodies to engage the expansion part in a more anatomical configuration.

Turning to another embodiment, the ankle brace has a calf body which defines first and second frontal sides spaced by an opening. The brace also includes opposed first and second ankle struts pivotally attached to the calf body. A footplate is connected to the ankle struts, and the footplate has a main body and a peripheral edge portion attached to the main body. The peripheral edge portion has greater flexibility than the main body.

In a variation, the peripheral edge portion has a variable width extending from the ankle struts to a toe portion of the footplate. The ankle struts and footplate may be integrally molded together such that the peripheral edge portion extends from the ankle struts and about a toe portion of the footplate.

In another variation, an under surface of the footplate defines a plurality of gripping protrusions formed from the peripheral edge portion. The peripheral edge portion is formed from a material having greater frictional properties than the main body.

According to an additional variation, the footplate defines a heel portion formed from a material having greater frictional properties than the main body. The heel portion defines a plurality of gripping protrusions formed on an under surface thereof.

The footplate may define a plurality of apertures, and a heel cup formed from a material having greater flexibility than the main body.

In yet another embodiment, the ankle brace has a calf body defining first and second frontal sides spaced by a clearance. The brace has opposed lateral and medial ankle struts pivotally attached to the calf body. A footplate is connected to the ankle struts. The medial ankle strut has greater rigidity than the lateral ankle strut.

Turning to another embodiment, the ankle brace includes a calf body defining lateral and medial sections spaced at corresponding frontal sides by a clearance. Opposed lateral and medial ankle struts are pivotally attached to the calf body, and a footplate is connected to the ankle struts. The calf body medial section has greater rigidity than the calf body lateral section.

A variety of different strapping configurations are available for the embodiments of the ankle brace to accommodate different levels of support and activity by the wearer. The ankle brace itself is arranged to receive a variety of different strapping systems, which transform the brace so as to treat different foot and ankle stability conditions.

BRIEF DESCRIPTION OF THE DRAWINGS

FIG. 2 is a perspective view the ankle brace of FIG. 1 in a closed configuration.

FIG. 3 is a perspective view of the footplate of the ankle brace of FIG. 1.

FIG. 4 is a first rear perspective view of the ankle brace of FIG. 1.

FIG. 5 is a second rear perspective view of the ankle brace of FIG. 1.

FIG. 6 is a rear perspective view of an embodiment of a footplate for use in the ankle brace of FIG. 1.

FIG. 7 is a top plan view of an embodiment of a footplate for use in the ankle brace of FIG. 1.

FIG. 8 is a top plan view of an embodiment of a footplate for use in the ankle brace of FIG. 1.

FIG. 9A is a cross-sectional view taken along line IX-IX in FIG. 8.

FIG. 9B is a cross-sectional view of FIG. 9A in an expanded footplate configuration.

FIG. 10 is an elevational view of an embodiment of a support coupling for use in the ankle brace of FIG. 1.

FIG. 11 is a cut-away cross-sectional view taken along line XI-XI in FIG. 10.

FIG. 12 is a sectional elevational view of an embodiment of an expansion coupling system for use in the ankle brace of FIG. 1.

FIG. 13 is a sectional elevational view of an embodiment of an expansion coupling system for use in the ankle brace of FIG. 1.

FIG. 14 is a perspective view of a strapping arrangement for use in an ankle brace.

FIG. 15 is a perspective view of a strapping arrangement for use in an ankle brace.

FIG. 16 is a perspective view of a variation of a lateral side of an ankle brace.

FIG. 17 is another perspective view of a variation of a lateral side of an ankle brace.

FIG. 18 is yet another perspective view of a variation of a lateral side of an ankle brace.

FIGS. 19 and 20 are elevational views of a variation of padding lining the ankle brace.

FIG. 21 is a perspective view showing an embodiment of a coupling system.

FIG. 22 is a perspective view exemplifying adjustment of the coupling system according to FIG. 21.

DETAILED DESCRIPTION OF VARIOUS EMBODIMENTS

A. Overview

Figure 1:
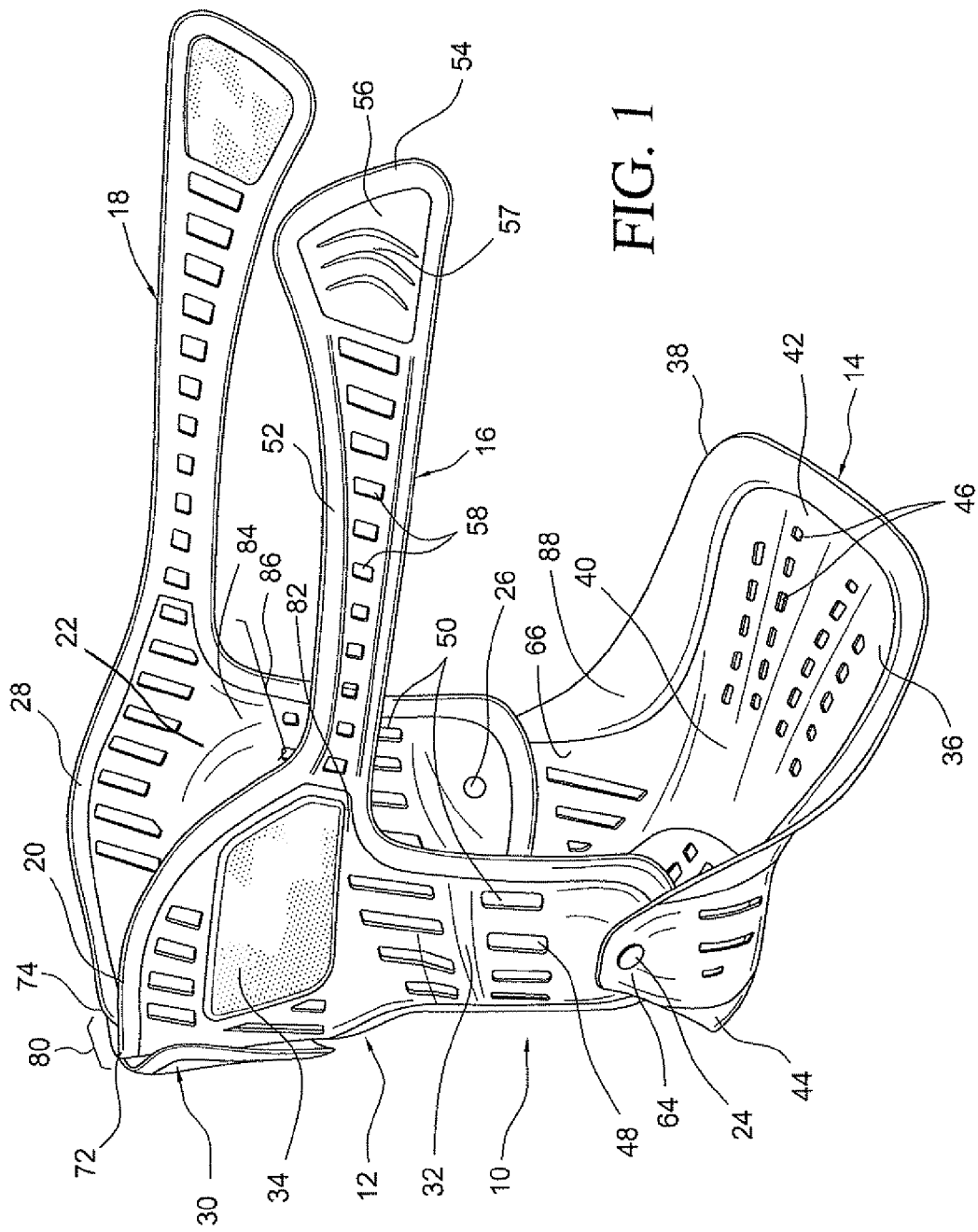
FIG. 1 is a perspective view of an embodiment of the ankle brace in an open configuration.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Various Embodiments of the Orthopedic Device in the Form of an Ankle Brace and Components for Use Therewith In accordance with a first embodiment of the invention, an ankle brace 10 is shown in FIGS. 1-5. The ankle brace defines a calf body 12 defining first and second frontal sides 82, 84 spaced by a frontal opening 86. Opposed first and second ankle struts 64, 66 pivotally attach to the calf body 12 and a footplate 14 connects to the ankle struts 64, 66.

First and second straps 16, 18 depend from the first and second frontal sides 82, 84 of the calf body 12, respectively. The first and second straps 16, 18 are arranged to extend juxtaposed across the opening 86 and to secure to the second and first frontal sides 84, 82, respectively. The first strap 16 extends below the second strap 18 when the straps are attached to corresponding sides of calf body 12.

The first and second straps have generally matching profiles. The first and second straps define first and second heights, respectively, which combine to form a cuff about the anterior side of a wearer's ankle. The combined cuff has a height that is greater than the individual first and second heights and allows the ankle brace to be securely attached to the ankle of the wearer.

According to this particular embodiment, the calf body 12 comprises first and second calf shells 20, 22, which are connected at first and second pivoting hinges 24, 26, respectively, to the first and second ankle struts 64, 66. The calf shells 20, 22 are formed from a substantially rigid or semi-rigid material, and are surrounded by a more flexible peripheral edge portion 28. The calf shells 20, 22 each define a bulge 32 generally corresponding to the malleolus of the wearer and are located near the first and second pivoting hinges 24, 26.

The pivoting hinge corresponding to the medial side of the ankle is located at a position higher than the side corresponding to the lateral side of the ankle. Therefore, the medial strut extends longer than the lateral strut.

The first and second calf shells 20, 22 each define wing-like first and second rear sides 72, 74 spaced by a rear opening 80. An expansion coupling 30 is adjustably secured to the first and second rear sides 72, 74 thereby bridging the rear opening 80, and providing an adjustment of and fixing the width of the opening 80. The rear sides 72, 74 each define a plurality of receiving slots 78 of which the expansion coupling 30 can engage to provide adjustment of the width of the opening 80 and therefore the fix a distance between the rear sides 72, 74.

The calf shells 20, 22 define a recess 34 located near the first and second frontal sides 82, 84 that accommodate a free end portion 54 of the second and first straps 18, 16, respectively. The recess 34 includes a loop receivable portion (not shown) which may comprise a patch of hook material or an integrally molded series of hooks that are adapted to engage loop material (not shown) located at the end portions of the first and second straps.

The footplate 14 defines a body section 36 having an arch portion 40 and a toe portion 42. It will be noted, however, that the toe portion 42 may not necessarily extend in length to encompass the wearer's toes. The footplate 14 also includes a heel portion 44 adjacent to the arch portion 40. The footplate 14 defines a plurality of apertures 46 along its length which provide a better circulation of air for the foot.

The body section 36 may be formed from a substantially rigid or semi-rigid material. A peripheral edge portion 38 extends from the first and second struts 64, 66, along the periphery of the arch portion 40 and about the toe portion 42. The peripheral edge portion 38 is substantially more flexible than the body section, and integrally and continuously secured to the body section 36 preferably without interruption. The peripheral edge portion 38 has a variable thickness such that an arch edge portion 88 is greater along the arch portion 40 and has a narrower width about the toe portion 42.

By being "without interruption," it is intended that the peripheral edge portion and the body section form substantially a unitary structure without any significant seam, thereby forming a continuous surface across both components. Moreover, the peripheral edge portion and the body section are integrally secured to one another.

The flexibility of the arch edge portion provides some structural support for the foot and further prevents movement of the foot due to its frictional properties. Further, the flexibility of the arch edge portion accommodates shoe sizes since it is movable relative to the body section of the footplate. The top surface of the footplate may be provided with an anti-skid feature, such as with various segments of an anti-skid material like PORON or silicone.

The calf shells, struts and footplate, and the corresponding peripheral edge portions may be constructed in any of the various manners described in pending U.S. application Ser. Nos. 12/068,781 and 12/153,389, both incorporated herein by reference.

The heel portion 44 is either formed from the same material as used to form the peripheral edge portion 38 or another material that is flexible and has cushioning properties. Similarly, the heel portion 44 defines a series of apertures 46, as with the arch portion 40 and the toe portion 42. According to this embodiment, the heel portion 44 is open thereby permitting adaptability to a shoe and accommodation of heel sizes.

On an undersurface of the arch and toe portions 40, 42, non-skid regions are formed along the peripheral edge portion 38 by way of raised protuberances 60. Likewise, an undersurface of the heel portion 44 also forms non-skid regions by way of raised protuberances 62. The non-skid regions are arranged to grip internal portions of a shoe to prevent slippage of the footplate 14 therein. The peripheral edge portion and the heel portion also attribute to providing a greater frictional surface for the foot, thereby minimizing or preventing movement of the foot relative to the footplate.

The calf shells 20, 22, and the struts 64, 66, define a plurality of slots 48, 70, respectively. These slots 48, 70 are adapted to provide ventilation to the ankle and foot of the wearer. Moreover, these slots 48, 70 may be likewise formed to receive certain strapping arrangements. For example, strut slots 50 formed on the first and second frontal sides are formed as D-rings so as to receive a strap that extends therebetween in order to provide greater security of the ankle brace on the ankle of the wearer (see for example FIG. 14). Other slots could be similarly adapted such as those located on the rear sides of the calf body.

The straps 16, 18 are preferably integrally molded and continuously formed with the calf shells 20, 22. Specifically, the straps 16, 18 have strap bodies 52 which are defined as elongate sections of the peripheral edge portion 28. These strap bodies 52 may be substantially more flexible than the calf shells 20, 22, and can allow for bending about the anterior of the wearer's ankle.

A handle insert 56 is integrally molded onto a free end portion 54 of the strap bodies 52, and is surrounded by the material forming such strap bodies 52. The handle insert 56 is formed from a material more rigid than the material used to form the strap bodies 52, and defines gripping regions 57 formed by ridges or other raised surfaces. The strap bodies 52 form a plurality of openings 58 thereby providing greater flexibility and ventilation of the straps 16, 18.

Turning to FIG. 6, a variation of the footplate 100 is shown. In this embodiment, the footplate 100 defines a body section 102 that is surrounded by a peripheral edge portion 112, and first and second struts 104, 106 connect to the footplate much in the same manner as in the footplate 12 in accordance with the ankle brace 10. The footplate 100 likewise defines an arch portion 108 and a toe portion 110. In this footplate 100, a plurality of elongate slots 114 are formed along the length of the footplate.

As for the heel portion 116, it is closed in that it includes a heel cup 118 thereby forming a closed heel portion. Preferably, the heel portion 116 is formed from the same material as the peripheral edge portion 112 thereby providing more flexibility. However, the heel portion 116 may also be constructed from a material that inherently provides some padding, or a substantially flexible material, or both. Alternatively, the heel portion 116 may be formed to have a thickness that is greater than the peripheral edge portion or the body portion, so as to allow for greater compressibility and therefore cushioning for the heel.

In observing FIG. 7, another variation of a footplate is shown having split sides. This footplate 122 includes first and second body portions 126, 128 which are connected to one another via the peripheral edge portion 128 and middle strip 130. As with the body portions of the prior embodiments, these first and second body portions 126, 128 are substantially rigid or semi-rigid. The peripheral edge portion 128 and the middle strip 130, on the other hand, are flexible relative to the first and second body portions 126, 128, thereby providing a split footplate that permits lateral-medial movement accommodation.

The footplate 122 includes a toe portion 132 formed by at least part of the peripheral edge portion 128 which is constructed with a greater width than in prior footplate embodiments. The peripheral edge portion 128, particularly at the toe portion 132, may have a tapered thickness so as to permit easier installation of the footplate in a shoe. The footplate 122 also defines a heel portion 134 which may be constructed in either an open or closed manner. Suitable anti-skid regions 136 are formed on the toe and heel portions 132, 134, and elongate or other suitably shaped anti-skid regions 138 are formed along the middle strip 130.

Another variation of a footplate 140 is depicted in FIG. 8 wherein the footplate has an adjustable width feature. The footplate 140 is divided into first and second body portions 144, 146 which are adjustable relative to one another along the dividing line 148. The first body portion 144 defines upper and lower locking heads 154, 160 which are engageable with a series of upper first and second keyholes 152, 156, and lower first and second keyholes 158, 162 formed on the second body portion 146.

According to this example, if the locking heads 154, 160 engage the upper and lower first keyholes 152, 158, the first and second body portions 144, 146 are flush with one another along the dividing line 148, as depicted in FIGS. 8 and 9A. On the contrary, in an expanded footplate configuration shown in FIG. 9B, if the locking heads 154, 160 engage the upper and lower second keyholes 152, 158, the first and second body portions 144, 146, a gap is formed over a ledge 164 of the first body portion upon which the locking heads are formed. The gap is filled with a transition strip 150 which is preferably formed from a flexible material having frictional, anti-skid properties. Alternatively, the transition strip 150 may be formed from a more rigid or semi-rigid material, similar to or the same as the material forming the first and second body portions.

By providing the transition strip 150, the under surface of the footplate can remain substantially flush with the corresponding surface of a shoe by forming a continuous surface. Further, the top surface of the footplate likewise forms a continuous surface by way of the transition strip, and the location of the locking heads within the keyholes. As for the unused keyholes, inserts may be provided that can be inserted into the unused keyholes to further improve continuity across the footplate surface.

Turning to the expansion coupling, FIG. 10 depicts a detailed view of the expansion coupling 30 used in the ankle brace 10. According to this variation, the expansion coupling 30 defines a coupling body 202, and locking tabs 204 formed on opposed sides adapted for adjustably securing with the receiving slots 78 formed on the first and second calf shells. The coupling body 202 forms a plurality of openings 206 adapted to provide ventilation to the wearer, and a peripheral edge portion 208 surrounds the coupling body 202, as in other embodiments described herein.

FIG. 11 illustrates a cross-section of the expansion coupling 30 wherein the locking tab 204 defines a post 210 and a head portion 212 which is adapted to fasten onto the calf shells via the receiving slots. The locking tab is not limited to the shape shown in FIG. 11, but may comprise any shape, such as hooks, that permit secure yet removable engagement with the receiving slots. Alternatively, the expansion coupling and the rear side of the calf shells may include a hook and loop system to retain the expansion coupling to the calf shells, thereby eliminating fixed sequential positions upon which the expansion coupling secures onto the calf shells. Further, each side of the expansion coupling may define a plurality of locking tabs or other suitable means for securing to the calf shells.

In a variation of the expansion coupling, FIG. 12 shows an expansion coupling system that eliminates an expansion coupling separate from the calf shells. According to this variation, the expansion coupling system 220 is defined by a first wing 226 depending from a first calf body rear side 222, and a second wing 228 depending from a second calf body rear side 224. The first wing 226 is arranged to overlap the second wing 228. The first wing 226 defines a locking tab 230 which can secure to a series of receiving slots 232 formed on the second wing 228. The first and second wings 226, 228 have matching peripheral edge portions 234, 236 which permit a continuous peripheral edge portion regardless of the position of the first and second wings relative to one another when they are interlocked.

In another variation of the expansion coupling, FIG. 13 shows an alternative which eliminates a separate expansion coupling. According to this variation, the expansion coupling system 240 is defined by a first wing 246 depending from a first calf body rear side 242, and a second wing 248 depending from a second calf body rear side 244. The first wing 246 is arranged to overlap the second wing 248. The first wing 246 defines a series of keyholes 252, 254 in which a locking tab 250 engages. Much like the expansion coupling system 220, the expansion coupling system 240 permits adjustability of the second wing 248 relative to the first wing 246.

The expansion coupling system 240 also exemplifies how the peripheral edge portion 256, 258 extending about the calf shells can have a greater width at the rear edge portion of the calf shells where they meet. Any of the expansion couplings described herein may include this feature, and likewise for those ankle braces of the invention omitting an expansion coupling such that the calf shells are not separated by instead a single calf body is provided.

This arrangement in FIG. 13 of the peripheral edge portion is particularly advantageous in that the peripheral edge portions 256, 258 join to provide enhanced pressure relief on the posterior portion of the wearer's ankle and in the Achilles region. This provides superior comfort to the wearer while the calf shells sufficiently provide the structural rigidity to secure the ankle. It will be noted that the second wing 248 has a peripheral edge portion extension 260 which accommodates the adjustment of the second wing 248 relative to the first wing 246.

Various supplementary strapping arrangements may be used in combination with any of the ankle brace embodiments described herein. For example, FIG. 14 shows a strapping arrangement for ankle brace 300 that provides "moderate" support. The ankle brace 300 has a calf body 302 including a main strap 304 like any one of the main straps described herein which extends over the upper anterior aspect of the ankle and secures to (or is integrally formed with at least one) opposed sides of the calf body.

The calf body 302 also forms a lower strap 306 which extends over the lower aspect of the ankle. While shown herein as being formed integrally with a peripheral portion of the calf body 302, as described in connection with other embodiments herein, the lower strap 306 may also be separately formed relative to the calf body, and secured via slots to the calf body. The ankle brace 300 also includes a heel strap 308 which secures to slots 309 formed on the calf body 302. However, the heel strap 308 may likewise be formed integrally with the calf body.

In another example, FIG. 15 depicts a "maximum" supplementary strapping system by way of strap 316 which secures to or is integrally formed with the calf body 312 and is in supplement to the main strap 314. The maximum strap 316 is intended to wrap about the ankle in a figure "8" type configuration, or any other serially wrapping configuration to provide enhanced support to the ankle.

Turning to the embodiments of FIGS. 16-18, the various ankle brace embodiments are focused on providing more inversion support than eversion support. These embodiments are designed with the concept in mind that ankles tend to provide better support through eversion than inversion.

For example, if one has a tubular brace place about an ankle, and the ankle is flexed into inversion, the medial side tends to go into compression. On the other hand, the lateral side tends to go into a stretch, tensile force. When ankle braces are very rigid on the lateral side, there is a risk that the lateral malleolus may dig into the rigid strut and considerable pressure is therefore exerted on the lateral malleolus.

The embodiments of FIGS. 16-18 propose to arrange the lateral calf portion and/or lateral ankle strut with greater softness or less rigidity than the medial calf portion and/or medial ankle strut. Preferably, the lateral calf portion and/or lateral ankle strut however provides little or no stretch. The stretch resistance on the lateral calf portion and/or lateral ankle strut would therefore aid in providing inversion control with the more rigid medial calf portion and/or medial ankle strut.

In observing the ankle brace 400 of FIG. 16, the lateral side of the ankle brace is shown with calf shell 402 and peripheral edge portion 404 constructed from a material having greater flexibility than the material forming the calf shell. The calf shell 402 includes a tapered portion 406 which reduces to the pivot point 410 whereat the ankle strut 408 secures. The ankle strut 408 includes a narrow frame portion 412 connecting at the pivot point 410 to the calf shell 402, and a more flexible peripheral edge portion 414 surrounding the frame portion 412. A footplate is connected or integrally formed with the ankle strut as in any one of the various footplate embodiments described herein.

Next, FIG. 17 shows an ankle brace 420 embodiment wherein the lateral calf portion 422 does not extend to the pivot point 430 connecting to the lateral ankle strut 428. Instead, a peripheral edge portion 424 extends along the lateral calf portion 422 and a malleolus region 426 continuous with the peripheral edge portion 424 connects at the pivot point 430. Similarly, the lateral ankle strut 428 includes a peripheral edge portion 432 which connects at the pivot point 430. A more rigid frame portion 430 of the ankle strut 428 is located below the pivot point 430, so that the malleolus region 426 and the peripheral edge portion 432 provide flexibility at a location generally corresponding to the lateral malleolus of the wearer.

Lastly, FIG. 18 illustrates an ankle brace 440 having a lateral calf portion 442 including a narrow portion 446 forming a head 458 at pivot point 450. A flexible peripheral edge portion 444 surrounds at least part of the lateral calf portion 442, and is more flexible than the lateral calf portion. The ankle strut 448 connects at the pivot point 450 to the lateral calf portion 442. The ankle strut 448 defines a head 456 formed from a material that is more rigid than a peripheral edge portion 452 which forms part of the ankle strut. A narrow strip 454 extends from the head 456 to connect to one of any of the footplates described herein. The narrow strip 454 is more rigid than the peripheral edge portion 452.

In each of the embodiments of FIGS. 16-18, the ankle brace is tailored to provide greater flexibility on the lateral side of the brace, but yet without stretch. The embodiments serve therefore to provide more inversion support than eversion support.

FIGS. 19 and 20 exemplify embodiments of liners which may be secured to the inner surface of the ankle brace.

FIG. 19 shows a medial liner 500 which includes a strap portion 502, a shell portion 504 and coupling portion 506. The strap portion 502 is sized so as to correspond to both of the straps protruding out from the anterior side of the ankle brace. For example, a segment of the medial strap is secured (detachably or permanently) to the strap portion 502. When the medial strap is secured to the lateral frontal side, the strap portion 502 closes at least part of the front opening. The lateral strap will likewise extend over the strap portion 502 as it is secured to the medial frontal side.

The strap portion 502, as may the shell portion 504 and the coupling portion 506, includes variations in thickness forming indentations 508 so as to facilitate bending as the strap portion 502 extends over the front opening, and also to ease trimming of the liner to size.

The coupling portion 506 is configured to extend across the rear opening, and corresponds to the coupling system, such that the coupling system overlies the coupling portion 506.

FIG. 20 shows a lateral liner 510 which includes a strap portion 512, shell portion 514 and coupling portion 516. The strap portion 512 is arranged to at least overlap the strap portion 502 of the medial liner 500, and the coupling portion 516 is arranged to overlap the coupling portion 506 of the medial liner (as depicted in FIG. 22).

The liners may be formed from a variety of materials. In an exemplary variation, the liners are thermoformed (for imparting the particular indentations) closed cell foam with hook receivable (or vice versa) material adapted to secure to the shell of the ankle brace. In order to reduce the bulk of the liner, the liners may be easily trimmed at appropriate indentations under the closure straps and at any other locations on the liners.

Turning to FIGS. 21 and 22, an embodiment of a coupling system is depicted. In this coupling system 520, an expansion part 522 includes opposed series of diagonal slots 528, such that there are first and second series of slot arranged obliquely relative to one another. Each of the calf body rear sides form a tab 524, 526 on an inner surface thereof which extend toward one another. These tabs are arranged to engage and secure with one of the slots 528 for size adjustment of the calf portion of the ankle brace. The oblique arrangement of the slots allows for the calf bodies to engage the expansion part in a more anatomical configuration.

The expansion part 522 defines a trapezoidal shape 530, which in combination with the diagonal slots, allows for the rear portion of the ankle brace to closely conform to the standard conical shape of the lower calf of the wearer, thereby forming an anatomically correct shape.

The expansion part may include a plurality of indicia corresponding to the slots so as to indicate settings for the expansion coupling. For example, slots denoted by "1" are for small calves, slots denoted by "2" are for medium calves (such as standard sized calves), and slots denoted by "3" are for large sized calves.

Figure 23:
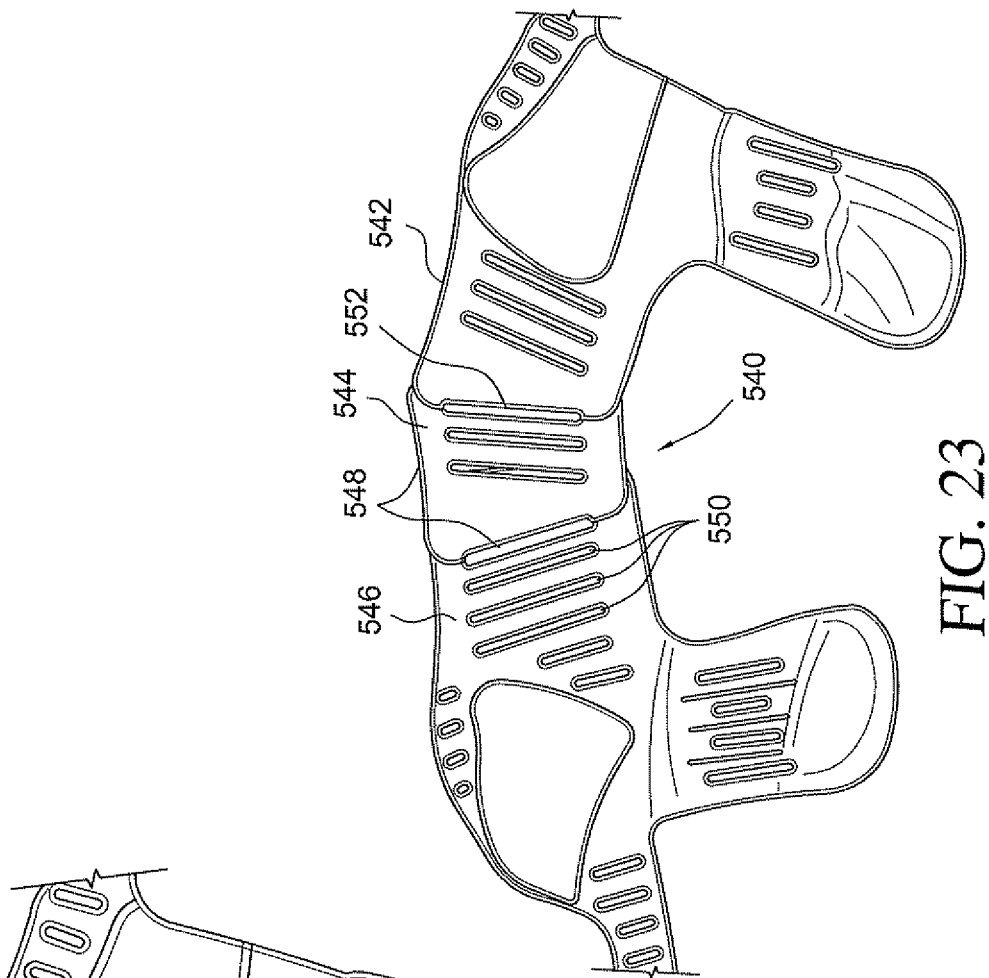
FIG. 23 is a perspective view showing an embodiment of a coupling system.
Figure 24:
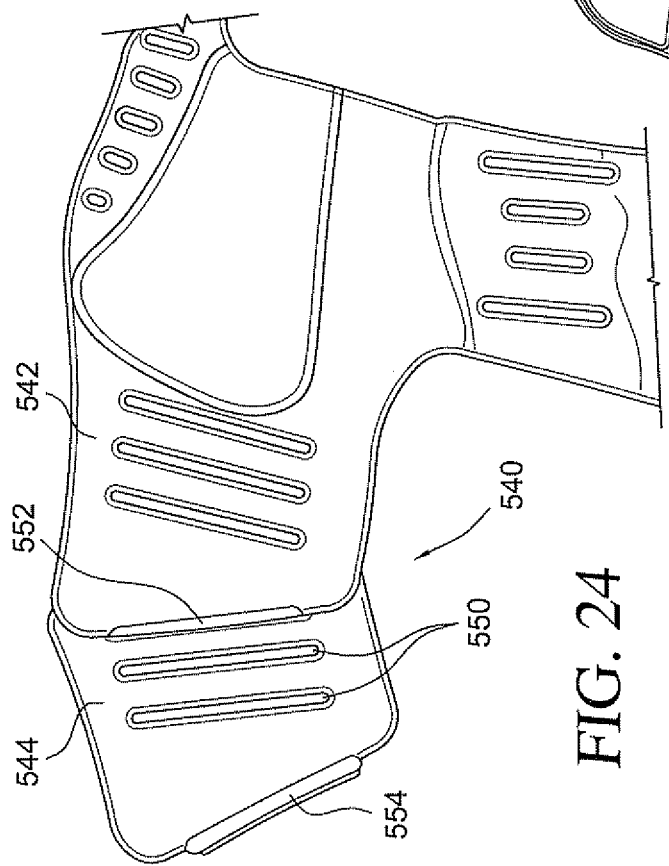
FIG. 24 is a perspective view exemplifying adjustment of the coupling system according to FIG. 23.

In observing FIGS. 23 and 24, an embodiment of a coupling system is depicted. According to this coupling system 540, the calf body rear sides form extensions 542, 546, which may be secured directly to one another, or secured to one another via an extension part 544. The extension 542 includes a tab 552 which is engageable with one of the series of slots formed in either the expansion part 544 (slots 556) or the extension 546 (slots 550). The extension part 544 likewise defines a tab 554 which is engageable one of the slots 550 in the extension 546.

As can be seen from at least FIG. 24, the extensions and the extension part form a shape which is different from a straight shape, such that the angled contour of the shape is adapted to more closely to anatomical shape of a wearer's calf.

In observing FIGS. 25-28, a variety of different strapping configurations are available for the embodiments of the ankle brace to accommodate different levels of support and activity by the wearer. The ankle brace is modular in that these different strapping configurations transform the basic ankle brace (without the strapping configurations) to treat different foot and ankle stability conditions.

Figure 25:
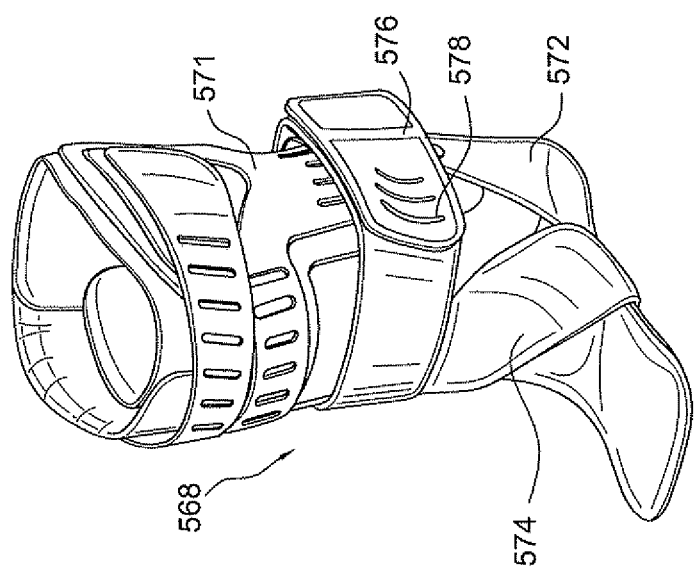
FIG. 25 is a perspective view showing the ankle brace with a stability strap in a strapping configuration.

FIG. 25 shows an embodiment of the ankle brace 568 with a calf portion 571 pivotally connected to the foot portion 572, such that a stability strap 574 secures to both the calf and foot portions 571, 572 and wraps thereabout. A first end of the stability strap 574 includes a securing element 576 which is adapted to secure to any portion of the stability strap 574 or to appropriate portions of the calf and foot portions 571, 572.

In a preferred embodiment, the securing element 576 includes an engaging portion 578 having hook elements which releasably secure to hook receiving material on the stability strap or at locations on the calf and foot portions. Further, the securing element may be constructed from a rubber-type material tougher and stronger than the material used to construct the stability strap. Preferably, the stability strap is formed from a textile having an outer surface which is hook engageable.

Figure 26:
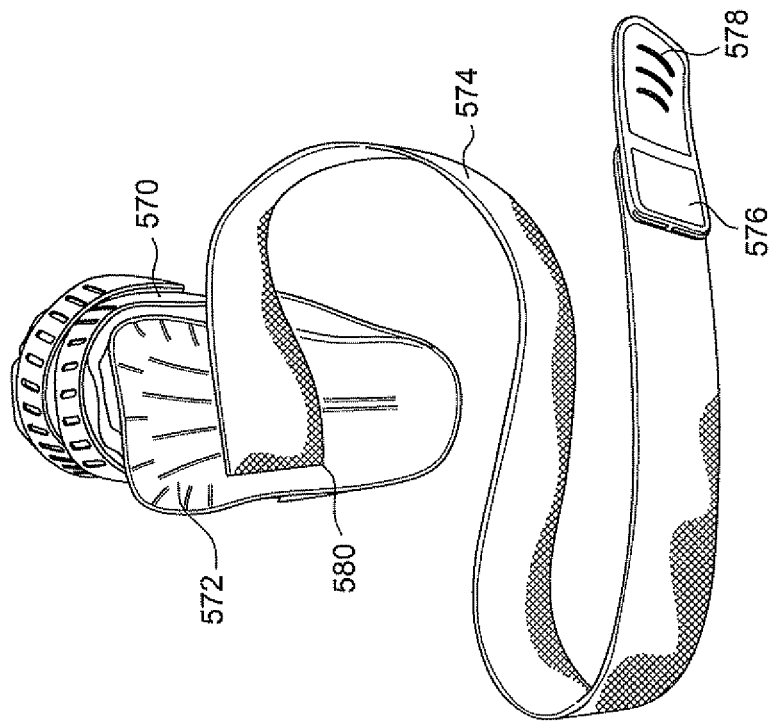
FIG. 26 is a perspective view showing the ankle brace with a stability strap secured to an undersurface of the footplate.

FIG. 26 depicts a second end of the stability strap 574 attaching to a bottom portion of the foot portion 572 at a securing location 580 so that the strap is arranged for wrapping around the foot of the wearer in a particular configuration. It will be noted that the securing location may include hook elements which engage the hook receiving material of the stability strap.

Figure 27A:
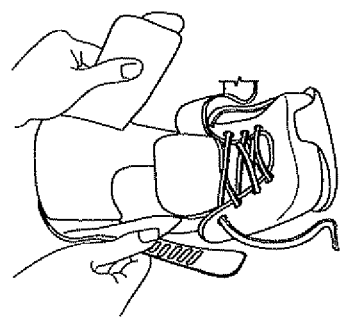
FIGS. 27A-27F are schematic views showing adjustment and donning of the ankle brace in a first strapping configuration.
Figure 27B:
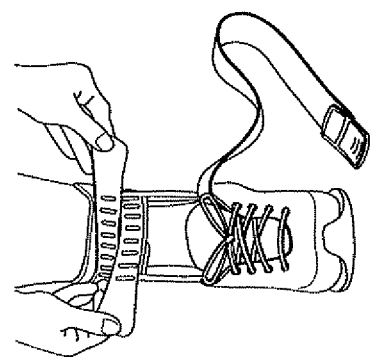
Figure 27C:
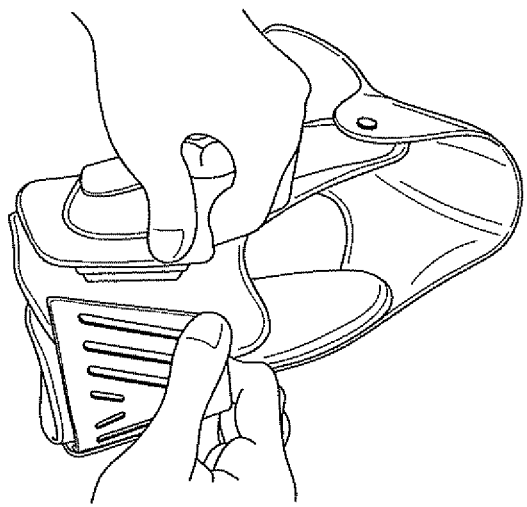

FIGS. 27A-27F exemplify a method for applying the brace onto the foot and ankle of the wearer. FIG. 27A shows that the ankle brace is inserted into a shoe, and that the dual closure straps of the brace are opened, with the stability strap extending out of the shoe with an end of the strap connected to the foot portion of the ankle brace (as depicted in FIG. 26). FIG. 27B shows that the foot is placed into the shoe and the shoe laces are tied. The dual closure straps are crossed, wrap over corresponding sides of the calf portion of the brace, and secured to the calf portion. FIG. 27C illustrates how prior to placing the ankle brace into the shoe or thereafter, the expansion coupling may be adjusted according to the circumference of the calf of the wearer.

Figure 27D:
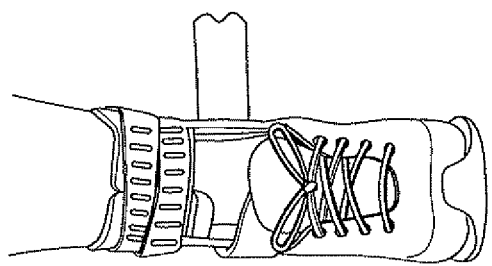
Figure 27E:
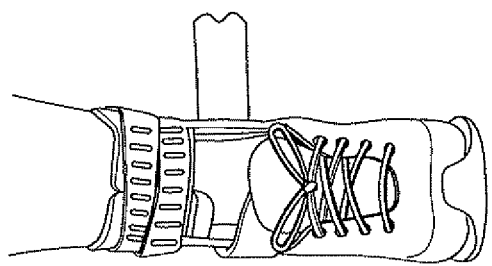
Figure 27F:
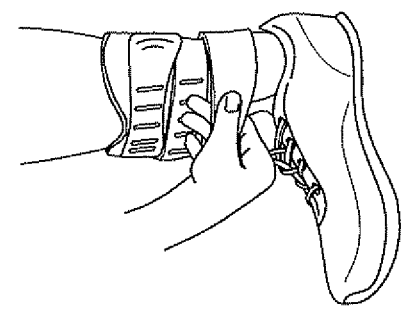

Turning to FIG. 27D, the stability strap is crossed over the top of foot, whereas in FIG. 27E the stability strap is snugly wrapped around and behind the ankle. FIG. 27F shows the securing element as being fastened down onto the stability strap so as to maintain the stability strap in place.

FIGS. 28A-28L exemplify varying strapping configurations which are possible to provide foot stability and ankle medial-lateral (ML) stability. The strapping configurations also vary according to ease of application. The arrangement of the ankle brace and the stability strap afford these various configurations with minimal modifications, and thus allows for a highly versatile brace without the need for individualized softgood elements, wraps, straps and other known optional items used for providing additional support to the ankle.

Because a complicated softgood support is not used, and instead only a strap is employed, the ankle brace is easily adapted for various stability settings, and is likewise more ventilated than prior art ankle braces. Greater forces may be exerted on the ankle and foot by the stability strap than in known softgood systems due to the easy tensioning of a single strap. Thus, the stability strap allows for comfortable circumferential conformity to the anatomy of the foot and ankle, superior breathability, and weight reduction of the brace.

Figure 28A:
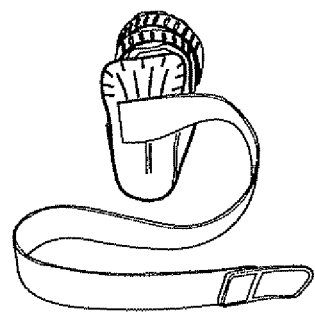
FIGS. 28A-28L are schematic views showing adjustment and donning of the ankle brace in multiple strapping configurations.

In a first configuration shown in FIG. 28A, which may be considered as a default configuration, the stability strap begins at the bottom of the footplate and wraps over the inside of the foot, and then around the ankle (as shown in FIG. 27F). This configuration provides moderate foot and ankle ML stability.

Figure 28B:
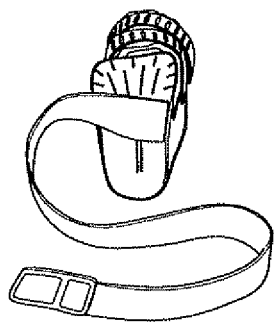
Figure 28C:
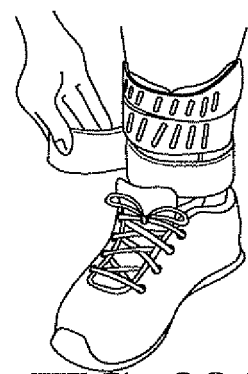

In a second configuration, shown by way of FIGS. 28B and 28C, the strap initiates from the bottom of the footplate and wraps up over the outside of the foot, and then about the ankle. This configuration has lower foot stability and moderate ankle ML stability.

Figure 28D:
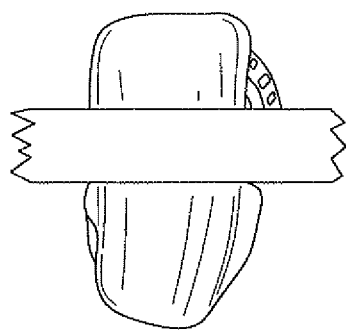
Figure 28E:
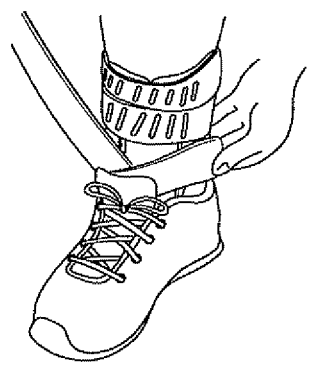
Figure 28F:
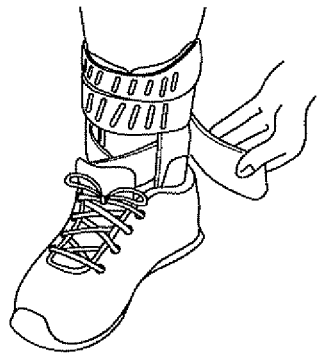

In a third configuration, as exemplified in FIGS. 28D-28F, an additional hook element is applied to the inner ankle strut. The middle of the strap is secured to the bottom of the footplate, and both ends of the stability strap cross over the top of the foot, and subsequently wrap about the ankle. This configuration provides enhanced foot stability, and moderate ankle ML stability.

Figure 28G:
Figure 28H:
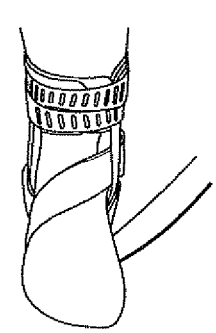
Figure 28I:
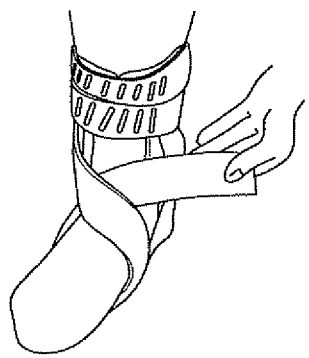

In a fourth configuration, as exemplified in FIGS. 28G-28H, an additional hook element is applied to the inner ankle strut. The stability strap initiates from the inside of the lower strut (FIG. 28G), and wraps around the outside of the foot, under the footplate (FIG. 28H), up across the top of the foot, and then around the ankle (FIG. 28I). This configuration provides enhanced foot stability and moderate ankle ML stability.

Figure 28J:
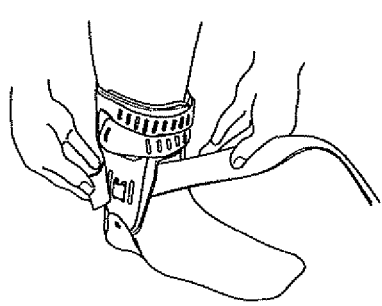
Figure 28K:
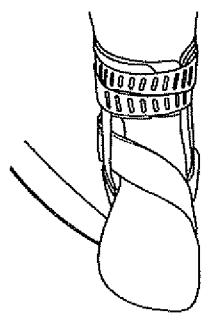
Figure 28L:
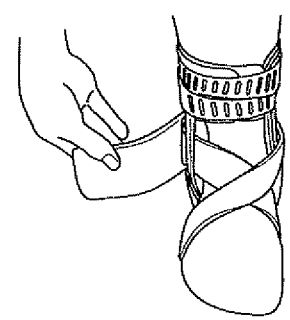

In a fifth configuration, as exemplified in FIGS. 28J-28L, an additional hook element is applied to the outer ankle strut (FIG. 28J). The stability strap wraps around the outside of the foot, under the footplate (FIG. 28K), up across the top of the foot, and then around the ankle (FIG. 28L). This configuration provides superior foot stability and enhanced ankle ML stability.

Figure 29:
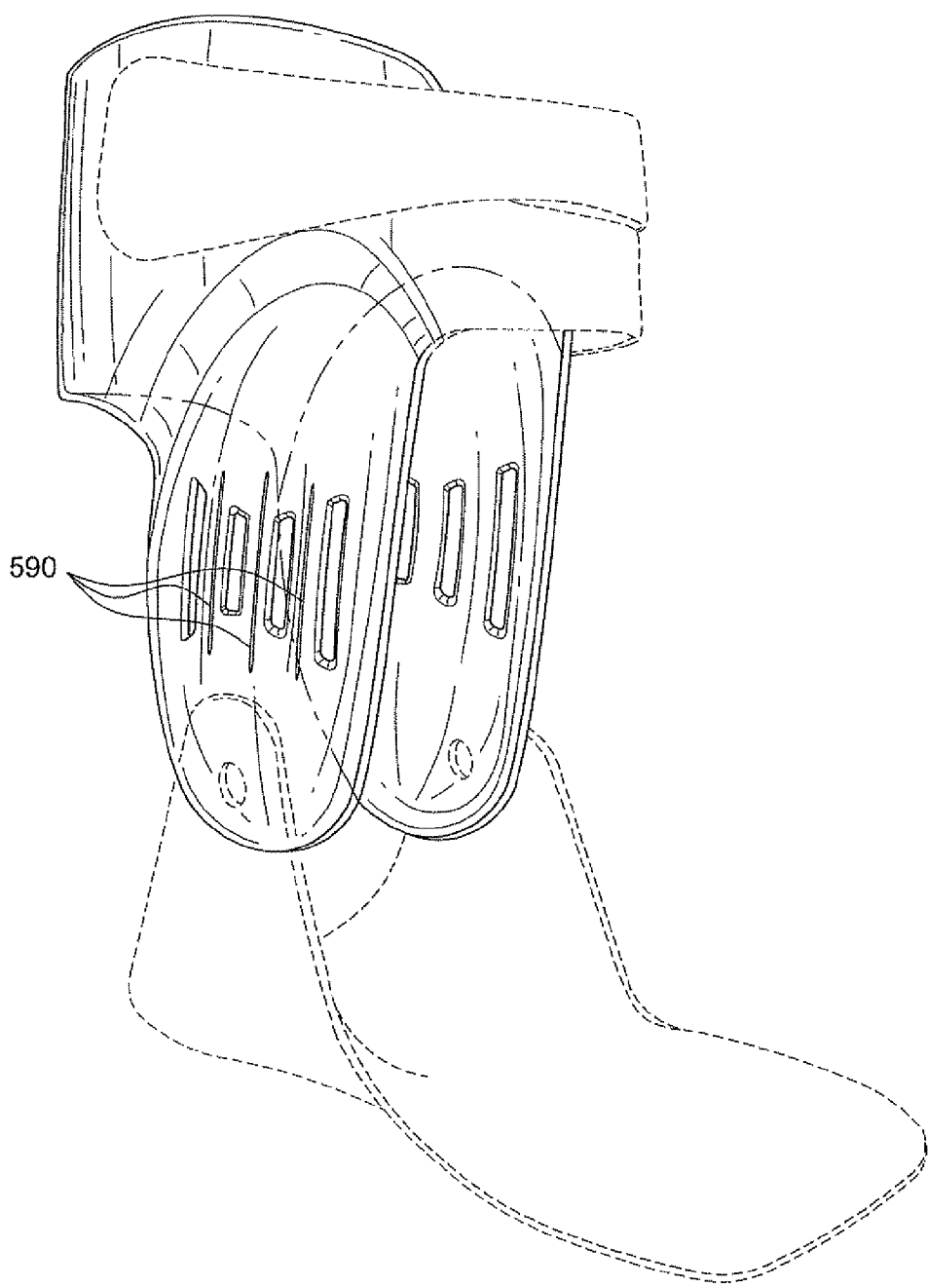
FIG. 29 is a perspective view of a variation of a lateral side of an ankle brace.

FIG. 29 shows an example of the ankle brace having a plurality of strengthening ribs 590 which may be formed along the ankle struts so as to provide enhanced inversion and eversion resistance. Moreover, the bottom portion of the footplate may include a texture that provides slip-resistant properties, thereby preventing rotation between the brace and the inside of the shoe.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct an orthosis in accordance with principles of the present invention. Additionally, it will be understood by the skilled artisan that the features described herein may be adapted to other types of orthopedic devices. Hence this disclosure and the embodiments and variations thereof are not limited to ankle braces, but can be utilized in any orthopedic devices.

Although this invention has been disclosed in the context of certain exemplary embodiments and examples of an ankle brace, it therefore will be understood by those skilled in the art that the present invention extends beyond the specifically disclosed ankle brace embodiments to other alternative embodiments and/or uses of the invention and obvious modifications and equivalents thereof. Thus, it is intended that the scope of the present invention herein disclosed should not be limited by the particular disclosed embodiments described above, and may be extended to orthopedic devices and supports, and other applications that may employ the features described herein.

The invention claimed is

1. An ankle brace, comprising:
a calf body defining opposed first and second frontal sides spaced by a frontal opening;
first and second straps depending from an upper portion of the first and second frontal sides of the calf body, respectively, the first and second straps being arranged to extend juxtaposed across the opening and secure to the second and first frontal sides, respectively;
wherein the first and second straps have generally matching profiles and combine to form a generally continuous cuff across the frontal opening;
wherein the first strap is continuously and unitarily formed from the first frontal side of the calf body, the second strap is continuously and unitarily formed from the second frontal side of the calf body;
wherein the first and second straps have first and second heights, respectively, and form a combined strap height greater than the first and second heights when the first and second straps secure to the second and first frontal sides, respectively.

2. The ankle brace according to claim 1, further comprising:
opposed ankle struts pivotally attached to the calf body; and
a footplate connected to the ankle struts.

3. The ankle brace according to claim 2, wherein the second strap depends from the second frontal side at a location higher relative to the footplate than a location from which the first strap depends from the first frontal side.

4. The ankle brace according to claim 1, wherein the calf body defines a shell portion and a peripheral edge portion secured to the shell portion, the shell portion having greater rigidity than the peripheral edge portion.

5. The ankle brace according to claim 1, wherein the first and second straps define a strap body and a handle, the handle being integrally molded into the strap body.

6. The ankle brace according to claim 5, wherein the strap body is formed from a material more resilient than a material used to form the handle.

7. The ankle brace according to claim 6, wherein the handle defines a grip pattern.

8. The ankle brace according to claim 1, wherein the first and second straps define a plurality of apertures.

9. The ankle brace according to claim 1, wherein the first and second straps are arranged generally parallel heightwise relative to one another about the opening.

10. An ankle brace, comprising:
a calf body defining opposed first and second frontal sides spaced by a frontal opening;
a first strap depending from an upper portion of the first frontal side of the calf body and having a first free end arranged to secure to the second frontal side, a second strap depending from the upper portion of the second frontal side of the calf body and having a second free end arranged to secure to the first frontal side, the first and second straps arranged to extend juxtaposed across the opening and secure to the second and first frontal sides, the first and second straps having generally matching profiles and combining to form a generally continuous cuff across the frontal opening;
opposed ankle struts pivotally attached to a lower portion of the calf body; and
a footplate connected to the ankle struts;
wherein the second strap depends from the second frontal side at a location higher relative to the footplate than a location from which the first strap depends from the first frontal side, the first strap securing to the second frontal side and the second strap securing to the first frontal side of the calf body;
wherein the first and second straps have first and second heights, respectively, and form a combined strap height greater than the first and second heights when the first and second straps secure to the second and first frontal sides, respectively.

11. The ankle brace according to claim 10, wherein the first and second straps are continuously and unitarily formed from the calf body.

12. The ankle brace according to claim 10, wherein the first and second straps define a strap body and a handle integrally molded into the strap body.

13. The ankle brace according to claim 10, wherein the first and second straps define a plurality of apertures.

14. The ankle brace according to claim 10, wherein the first and second straps are arranged generally parallel heightwise relative to one another about the opening and extend in opposed directions across the opening.

15. The ankle brace according to claim 10, wherein the first frontal side defines a first recessed section upon which the second free end of the second strap secures, the second frontal side defines a second recessed section upon which the first free end of the first strap secures.

16. An ankle brace, comprising:
a calf body defining opposed first and second frontal sides spaced by a frontal opening;
a first strap depending from an upper portion of the first frontal side of the calf body and arranged to adjustably secure to the second frontal side, a second strap depending from the upper portion of the second frontal side of the calf body and arranged to adjustably secure to the first frontal side, the first and second straps arranged to extend juxtaposed across the opening and secure to the second and first frontal sides, the first and second straps have generally matching profiles and combine to form a generally continuous cuff across the frontal opening;
opposed ankle struts pivotally attached to a lower portion of the calf body;
a footplate connected to the ankle struts, said frontal opening extending from the calf body to a top surface of the footplate;
a stability strap having a first end secured to a bottom surface of the footplate and extending about at least one of the ankle struts and the first and second frontal sides below the first and second straps, the stability strap extending in the frontal opening between the cuff and the footplate;
wherein the first and second straps have first and second heights, respectively, and form a combined strap height greater than the first and second heights when the first and second straps secure to the second and first frontal sides, respectively.

17. The ankle brace according to claim 16, wherein the stability strap has a hook engageable outer surface and a second end including an engaging portion adapted to secure to the hook engageable outer surface.

18. The ankle brace according to claim 16, wherein the stability strap extends at an angle from a first side of the footplate to the ankle strut corresponding to a second side of the footplate across the opening.

19. The ankle brace according to claim 16, wherein the first and second straps are continuously and unitarily formed from the calf body.

20. The ankle brace according to claim 16, wherein the first and second straps are arranged generally parallel heightwise relative to one another about the opening and extend in opposed directions across the opening.

* * * * *